(12) United States Patent
Nissinen et al.

(10) Patent No.: US 11,965,838 B2
(45) Date of Patent: Apr. 23, 2024

(54) PORTABLE ASSESSMENT KIT AND METHOD FOR MEASURING METAL CONTENT OF AQUEOUS SOLUTION

(71) Applicant: 3AWater Oy, Kuopio (FI)

(72) Inventors: Tuomo Nissinen, Kuopio (FI); Tommi Tiihonen, Kuopio (FI); Joakim Riikonen, Kuopio (FI); Vesa-Pekka Lehto, Siilinjärvi (FI); Pekka Savolahti, Vantaa (FI)

(73) Assignee: 3AWater Oy, Kuopio (FI)

( * ) Notice: Subject to any disclaimer, the term of this patent is extended or adjusted under 35 U.S.C. 154(b) by 309 days.

(21) Appl. No.: 17/627,182

(22) PCT Filed: Jul. 13, 2020

(86) PCT No.: PCT/EP2020/069789
§ 371 (c)(1),
(2) Date: Jan. 14, 2022

(87) PCT Pub. No.: WO2021/013612
PCT Pub. Date: Jan. 28, 2021

(65) Prior Publication Data
US 2022/0268716 A1     Aug. 25, 2022

(30) Foreign Application Priority Data
Jul. 23, 2019   (FI) ...................... 20195649

(51) Int. Cl.
*G01N 23/223*   (2006.01)
*G01N 1/14*     (2006.01)
*G01N 1/40*     (2006.01)
*G01N 33/18*    (2006.01)

(52) U.S. Cl.
CPC ............. *G01N 23/223* (2013.01); *G01N 1/14* (2013.01); *G01N 1/405* (2013.01); *G01N 33/18* (2013.01);
(Continued)

(58) Field of Classification Search
CPC ........ G01N 23/223; G01N 1/14; G01N 1/405; G01N 33/18; G01N 2223/076;
(Continued)

(56) References Cited

U.S. PATENT DOCUMENTS

| 4,606,824 A | 8/1986 | Chu et al. |
| 5,416,028 A | 5/1995 | Stone |

(Continued)

FOREIGN PATENT DOCUMENTS

| GB | 2353860 B | 2/2004 |
| GB | 2400174 A | 10/2004 |
| JP | H0324459 A | * 2/1991 | ............. G01N 35/02 |

OTHER PUBLICATIONS

Australian Government; IP Australia, Examination report No. 1, Application No. 2020316612, dated Nov. 18, 2022, 5 pages.

(Continued)

*Primary Examiner* — Kiho Kim
(74) *Attorney, Agent, or Firm* — Ziegler IP Law Group (57) ABSTRACT

A portable assessment kit for measuring metal content of an aqueous solution. The kit includes a sample container having an opening at its first end for containing a sample of the aqueous solution, a disc holder having a first end for detachably attaching the disc holder to the opening of the sample container, a pre-concentration disc for collecting metals and being arrangeable in the disc holder. The pre-concentration has a first side and a second side. The kit further includes means for pumping the sample through the opening of the sample container to the first side of the pre-concentration disc and a measurement device for measuring amount of metals in the pre-concentration disc.

11 Claims, 6 Drawing Sheets

(52) U.S. Cl.
 CPC . *G01N 2223/076* (2013.01); *G01N 2223/507* (2013.01)

(58) Field of Classification Search
 CPC ......... G01N 2223/507; G01N 33/1813; G01N 21/25; G01N 23/083; B01J 20/0251; B01J 20/28054; B01J 20/282; B01J 20/3242; C02F 1/28; G01J 3/0272
 See application file for complete search history.

(56) References Cited

U.S. PATENT DOCUMENTS

| | | |
|---|---|---|
| 5,912,180 A | 6/1999 | Stone |
| 7,016,462 B1 | 3/2006 | Keville et al. |
| 2006/0257992 A1 | 11/2006 | McDevitt et al. |

OTHER PUBLICATIONS

Hou et al. "Determination of Trace Metals in Drinking Water Using Solid-Phase Extraction Disks and X-ray Fluorescence Spectrometry", Applied Spectroscopy, vol. 57, No. Mar. 3, 2003, XP055740117, ISSN: 0003-7028, DOI: 10.1366/000370203321558263, 6 pages.

International Search Report and Written Opinion, European Patent Office, Application No. PCT/EP2020/069789, dated Oct. 30, 2020, 15 pages.

Van Grieken et al., "Chelex-100 Ion-Exchange Filter Membranes for Preconcentration in X-ray Fluorescence Analysis of Water" Analytical Chemistry, vol. 49, No. 9, Aug. 1977, XP055740959 ISSN: 003-2700, DOI: 10.1021/ac50017a011, 6 pages.

\* cited by examiner

PORTABLE ASSESSMENT KIT AND METHOD FOR MEASURING METAL CONTENT OF AQUEOUS SOLUTION

TECHNICAL FIELD

The present disclosure relates generally to qualitative and quantitative assessment of aqueous solutions; and more specifically, to systems for assessing metal content in aqueous solution. Moreover, the present disclosure relates to methods for assessing metal content in aqueous solution.

BACKGROUND

With growing number of activities performed in proximity of water bodies, colossal amount of impurities has made its way into the water bodies. Notably, metals are introduced in the water bodies owing to natural and anthropogenic activities, such, weathering of soils and rocks, volcanic eruptions, mining, disposal of industrial wastes in the water bodies, disposal of metal pollutants in the water bodies, and the like. Therefore, there is a growing need for continuous monitoring of the water bodies for quality assessment thereof against such metals.

Generally, for assessment of quality of an aqueous solution, a sample of water from a water body is taken to a laboratory for assessment thereof. Several tests are performed onto the sample of water in the laboratory, using measurement devices, to determine a quality of the sample of water. However, such measurement devices are bulky, expensive, complex to handle, and slow to operate. Moreover, such measurement devices are prone to generating inaccurate results. Subsequently, the measurement devices are not reliable and cannot be employed in field conditions (namely, on-site of the water body) owing to heavy and bulky construction, complexity, and high sensitivity thereof.

Recently, filter-like solid phase extraction discs are being employed to collect metals present in sample of water from the water body. Furthermore, these discs are examined using measurement tools to determine a quality of the water body. However, handling of such discs is difficult owing to small size, fragile nature and very high risk of contamination associated therewith. Therefore, results generated by employing such discs outside laboratories are prone to errors. Additionally, obtaining accurate result on quality of the water body requires precise positioning of a discs in a measurement tool for examination thereof, wherein any deviation from precise positioning leads to an error in a result generated. Moreover, sorption of metals by the discs, from the sample of water, is dependent on conditions of the sample such as volume, flow rate, and the like. Therefore, varying conditions yield a variance in measurement parameters thereby yielding incorrect result. Furthermore, such tools to control the conditions are not portable on-site owing to requirement of electricity, running water, pumps, measurement units, and the like, for operation thereof. Subsequently, such process of examination of the discs in laboratories is tedious and time-consuming, and further requires technical experts for performing the examination of the discs. Furthermore, such systems employing the discs and the measurement tool further employs a drying device for drying the metals sorbed on the disc before examination thereof, by the measurement tools. Such drying devices further make the process inconvenient, cumbersome and increases time for examination of the disc. It is to be noted that sorption is to be understood as commonly used in the field, i.e. comprising absorption, adsorption and ion exchange.

Therefore, in light of the foregoing discussion, there exists a need to overcome the aforementioned drawbacks associated with the conventional systems for assessing quality of a sample of water from water bodies.

SUMMARY

The present disclosure seeks to provide a portable assessment kit for measuring metal content of an aqueous solution. The present disclosure also seeks to provide a method for measuring metal content of an aqueous solution. The present disclosure seeks to provide a solution to the existing problem associated with time and labour intensive processes for measuring metal content of an aqueous solution using conventional laboratory tools. An aim of the present disclosure is to provide a solution that overcomes at least partially the problems encountered in prior art, and provides an easy to operate portable assessment kit for on-site measurement of metal content in aqueous solution.

In one aspect, an embodiment of the present disclosure provides a portable assessment kit for measuring metal content of an aqueous solution, the portable assessment kit comprising:
  a sample container for containing a sample of the aqueous solution to be assessed, wherein the sample container comprises an opening at its first end for receiving the sample;
  a disc holder having a first end, and a second end opposite to the first end, wherein the first end of the disc holder is detachably attached to the opening of the sample container;
  a permeable pre-concentration disc for collecting metals, the pre-concentration disc having a first side, and a second side opposite to the first side, and being arrangeable in the disc holder;
  means for pumping the sample of the aqueous solution through the opening of the sample container to the first side of the pre-concentration disc and through the pre-concentration disc; and
  measurement means for measuring amount of metals in the pre-concentration disc, the measurement means being arrangeable in connection with the disc holder in such a manner that the first side of the pre-concentration disc is facing the measurement device.

In another aspect, an embodiment of the present disclosure provides a method for measuring metal content of an aqueous solution, wherein the method is implemented via a portable assessment kit, the method comprising:
  obtaining, in a sample container, a sample of the aqueous solution to be assessed, wherein the sample container comprises an opening at its first end for receiving the sample;
  pumping the sample of the aqueous solution through the opening of the sample container to a first side of a permeable pre-concentration disc and through the pre-concentration disc;
wherein the pre-concentration disc having a first side, and a second side opposite to the first side, is arrangeable in a disc holder; and
wherein the disc holder having a first end, and a second end opposite to the first end, is detachably attached to the opening of the sample container, via the first end of the disc holder; and measuring, using a measurement device, amount of metals in the pre-concentration disc, the measurement device being arrangeable in connection with the disc holder in such a manner that the first side of the pre-concentration disc is facing the measurement device.

Embodiments of the present disclosure substantially eliminate or at least partially address the aforementioned problems in the prior art, and enables accurate on-site assessment of aqueous solution thereby making a process of assessment of the aqueous uncomplicated and less time-intensive.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a portable assessment kit for measuring metal content of an aqueous solution, the portable assessment kit comprising:

a sample container for containing a sample of the aqueous solution to be assessed, wherein the sample container comprises an opening at its first end for receiving the sample;

a disc holder having a first end, and a second end opposite to the first end, wherein the first end of the disc holder is detachably attached to the opening of the sample container;

a permeable pre-concentration disc for collecting metals, the pre-concentration disc having a first side, and a second side opposite to the first side, and being arrangeable in the disc holder;

means for pumping the sample of the aqueous solution through the opening of the sample container to the first side of the pre-concentration disc and through the pre-concentration disc; and measurement means for measuring amount of metals in the pre-concentration disc, the measurement means being arrangeable in connection with the disc holder in such a manner that the first side of the pre-concentration disc is facing the measurement device.

In another aspect, an embodiment of the present disclosure provides a method for measuring metal content of an aqueous solution, wherein the method is implemented via a portable assessment kit, the method comprising:

obtaining, in a sample container, a sample of the aqueous solution to be assessed, wherein the sample container comprises an opening at its first end for receiving the sample;

pumping the sample of the aqueous solution through the opening of the sample container to a first side of a permeable pre-concentration disc and through the pre-concentration disc;

wherein the pre-concentration disc having a first side, and a second side opposite to the first side, is arrangeable in a disc holder; and wherein the disc holder having a first end, and a second end opposite to the first end, is detachably attached to the opening of the sample container, via the first end of the disc holder; and measuring, using a measurement device, amount of metals in the pre-concentration disc, the measurement device being arrangeable in connection with the disc holder in such a manner that the first side of the pre-concentration disc is facing the measurement device.

In yet another aspect, an embodiment of the present disclosure provides a portable assessment kit for measuring metal content of an aqueous solution, the portable assessment kit comprising:

a sample container for containing a sample of the aqueous solution to be assessed, wherein the sample container comprises an opening at its first end for receiving the sample;

a disc holder having a first end, and a second end opposite to the first end, wherein the first end of the disc holder is detachably attached to the opening of the sample container;

a permeable pre-concentration disc for collecting metals, the pre-concentration disc having a first side, and a second side opposite to the first side, and being arrangeable in the disc holder;

means for pumping the sample of the aqueous solution through the opening of the sample container to the first side of the pre-concentration disc and through the pre-concentration disc; and measurement means for measuring amount of metals in the pre-concentration disc, the measurement means being arrangeable in connection with the disc holder in such a manner that the first side of the pre-concentration disc is facing the measurement device, wherein the disc holder comprises a first part having the first end for detachably attaching the disc holder to the opening of the sample container, and the disc holder further comprises a second part and a third part, wherein the pre-concentration disc is arranged between the second part and the third part in a manner that the first side of the pre-concentration disc is facing the second part of the disc holder and the second side of the pre-concentration disc is facing the third part of the disc holder.

In still another aspect, an embodiment of the present disclosure provides a method for measuring metal content of an aqueous solution, wherein the method is implemented via a portable assessment kit, the method comprising:

obtaining, in a sample container, a sample of the aqueous solution to be assessed, wherein the sample container comprises an opening at its first end for receiving the sample;

detachably attaching a disc holder to the opening of the sample container, via a first part of the disc holder having a first end of the disc holder, wherein the disc holder has the first end and a second end opposite to the first end;

arranging a permeable pre-concentration disc between a second part of the disc holder and a third part of the disc holder in a manner that a first side of the pre-concentration disc is facing the second part of the disc holder and a second side of the pre-concentration disc is facing the third part of the disc holder, wherein the pre-concentration disc having the first side and the second side opposite to the first side is arrangeable in the disc holder;

pumping the sample of the aqueous solution through the opening of the sample container to the first side of the permeable pre-concentration disc and through the pre-concentration disc; and measuring, using a measurement device, amount of metals in the pre-concentration disc, the measurement device being arrangeable in connection with the disc holder in such a manner that the first side of the pre-concentration disc is facing the measurement device.

The present disclosure provides a portable assessment kit for measuring metal content of an aqueous solution and a method for measuring metal content of an aqueous solution. Typically, the portable assessment kit does not require established infrastructure such as electricity grids, water supply systems, and the like, for operation thereof. Subsequently, the portable assessment kit as described herein, operates to analyse a quality of the aqueous solution on-site, by determining an amount of metals present therein. Beneficially, the portable assessment kit allows on-site analysis of the aqueous solution thereby making the process of analysis of the aqueous solution less time-intensive and more economical by cutting down expenses relating to transfer and handling of the aqueous solution. Additionally, the portable assessment kit can be operated by an individual having ordinary skills, thereby cutting down operational costs associated with conventional assessment kits that require technical experts for operation thereof, and are further located in professional laboratories. Notably, the portable assessment kit comprises the pre-concentration disc arranged inside the disc holder. Subsequently, the disc holder prevents any damage such as contamination, careless handling, breakage, and the like, of the pre-concentration disc during use, storage and transportation in a field environment, thereby making an on-site operation thereof achievable. Thus, errors in measurement, arising due to contamination, careless handling or breakage of the pre-concentration disc, are prevented. Additionally, the disc holder enables precise positioning of the pre-concentration disc in the measurement device thereby allowing accurate and repeatable measurements to be recorded from the pre-concentration disc. Beneficially, the portable assessment kit as described herein, allows for analysis of quality of the aqueous solution by determining a level of metal therein, thereby preventing fatal hazards, for example, due to consumption of such aqueous solution (namely, water).

The term "pre-concentration disc", also used as "disc" for brevity is for example a solid phase extraction disk. Such solid phase extraction disc is capable of collection dissolved metal ions via sorption.

The portable assessment kit is employed for measuring metal content of the aqueous solution. Notably, "aqueous solution" refers to a solution, wherein a solvent of the solution is water ($H_2O$). It will be appreciated that the aqueous solution comprises substances present (namely, contaminants such as heavy metals) in water, wherein the substances are hydrophilic in nature. Optionally, the substances may be an acidic substance, a basic substance, a chelate, a complex or a salt. By a chelate and a complex are meant an organic compound onto which the metal is bound. Pursuant to embodiments of the present disclosure, the aqueous solution is a sample obtained from a water body. It will be appreciated that such aqueous solution from the water body comprises a plurality of substances dispersed in a large volume of water.

Throughout the present disclosure, the term "portable assessment kit" refers to a set of assessment tools employed for analysis of the sample of the aqueous solution. Specifically, the portable assessment kit is operable to collect the sample of the aqueous solution so as to perform analysis thereupon. Pursuant to embodiments of the present disclosure, the portable assessment kit performs quantitative or qualitative analysis on the sample of the aqueous solution to determine an amount of metals therein. The portable assessment kit is further operable to convert the quantitative data relating to metal content in the sample of the aqueous solution into qualitative analysis for the aqueous solution. It will be appreciated that determining an amount of metal content in the aqueous solution allows for analysis of, for example, if the aqueous solution is fit for human consumption, if the aqueous solution is fit for agricultural operations, if metal levels of discharge waters are below environmental regulations, to localize metal containing water leakages from industrial sites and/or to analyse when a water purification process is efficient enough.

The portable assessment kit comprises the sample container for containing the sample of the aqueous solution to be assessed, wherein the sample container comprises an opening for receiving the sample at its first end. Notably, the sample container enables collection of the sample of the aqueous solution from a large volume of water contained in water bodies (such as lakes, rivers) or water storage units (such as water tanks, water silos, reservoirs). In an example, the opening in the sample container may be immersed in the large volume of water to obtain the sample of the aqueous solution in the sample container. The sample container may also be in the form of a tube, open at both ends, its first end being used for receiving the sample and its second end being used for providing the sample to the pre-concentration disc.

Optionally, the sample container is a syringe, wherein the syringe comprises an opening at its first end and a piston at its second end. Notably, the first end and the second end are on the opposite ends of the syringe. The piston at the second end is driven from a first position to a second position in the syringe to generate a suction force enabling collection of the sample of the aqueous solution in the syringe through the opening at the first end of the syringe.

The portable assessment kit comprises the disc holder having a first end, and the second end opposite to the first end, wherein the first end of the disc holder is detachably attached to the opening of the sample container. Notably, the disc holder is a hollow unit of the portable assessment kit operable to hold the pre-concentration disc therein. Moreover, the first end of the disc holder is detachably attached to the opening of the sample container, thereby enabling a guided flow of the sample of the aqueous solution from the storage container to the pre-concentration disc. Additionally, the disc holder enables precise positioning of the pre-concentration disc therein so as to prevent inconsistent alignment of the pre-concentration disc for every reading. The precise positioning of the pre-concentration disc in the disc holder prevents misalignment of the pre-concentration disc in the measurement device thereby further preventing miscalibrations and inaccurate results. Moreover, the precise positioning of the pre-concentration disc in the disc holder prevents occurrence of inaccurate results owing to incorrect positioning thereof with respect to the flow of the sample of the aqueous solution. Beneficially, the disc holder prevents any damage to the pre-concentration disc by providing a protective covering thereto. Moreover, the disc holder prevents contamination of the pre-concentration disc due to field environments by isolating thereto from contaminants present on the field.

In an example, the disc holder has a defined opening for holding the pre-concentration disc therein. In another example, the disc holder is an arrangement of at least two constituent units, wherein the pre-concentration disc is arranged in a space between the at least two constituent units. Additionally, optionally, dimensions of the disc holder are adjustable so as to adjust varying dimensions of the pre-concentration disc therein. Moreover, optionally, the disc holder may comprise a plurality of auxiliary components for adjusting a dimension thereof, based on the dimensions of the pre-concentration disc.

The disc holder comprises a first part having a first end for detachably attaching the disc holder to the opening of the sample container. Specifically, the first part of the disc holder has the first end that detachably attaches the disc holder comprising the pre-concentration disc therein, to the opening of the sample container. In an instance, the first end of the first part of the disc holder and the opening of the sample container have threaded architecture to facilitate threaded attachment therebetween. In another instance, the first end of the first part of the disc holder is pushed inside the opening of the sample container to attach thereto.

The portable assessment kit comprises the pre-concentration disc for collecting metals, the pre-concentration disc having a first side, and a second side opposite to the first side, and being arrangeable in the disc holder. Notably, the pre-concentration disc enables sorption of contaminants (specifically, heavy metals) present in the sample of the aqueous solution, when the sample of the aqueous solution is passed through the pre-concentration disc. Herein, the pre-concentration disc is accommodated in the disc holder in a manner that its first side is facing towards the first end of the disc holder and its second side is facing towards the second end of the disc holder. Therefore, when the sample of the aqueous solution is received from the sample container by the disc holder, wherein the disc holder is attached to the opening of the sample container using its first end, the first side of the pre-concentration disc receives the sample of the aqueous solution that passes therethrough to the second side. Furthermore, the pre-concentration disc collects and concentrates the heavy metals therein, for qualitative and quantitative assessment thereafter.

The disc holder further comprises a second part and a third part, wherein the pre-concentration disc is arranged between the second part and the third part in a manner that the first side of the pre-concentration disc is facing the second part of the disc holder and the second side of the pre-concentration disc is facing the third part of the disc holder. Specifically, the pre-concentration disc is arranged between the second part of the disc holder and the third part of the disc holder. Beneficially, the second part and the third part of the disc holder protect the pre-concentration disc by safeguarding it against torsion arising during detachment of the first part of the disc holder from the opening of the sample container, during detachment of the first part from the second and the third part, and during arrangement of the measurement device in connection with the disc holder holding the pre-concentration disc. The second part and the third part also secure the pre-concentration disc in a fixed position during preconcentration. Moreover, the second part and the third part maintain the pre-concentration disc at a fixed position in relation to the measurement device during measurement, thereby leading to more reliable and accurate results.

Moreover, optionally, the second part and the third part of the disc holder are detachably attached to the pre-concentration disc using screw joints. The second part and the third part may also be detachably attached to the pre-concentration disc using any other type of connection, such as snap joints.

Optionally, the pre-concentration disc comprises of a material selected from a group of:
  a porous structure including a pore surface layer, wherein the pore surface layer comprises at least two atomic layers of at least one of the following: carbon, silicon carbide, silicon oxycarbide;
  a porous structure including a pore surface layer, wherein the pore surface layer comprises at least one metal binding ligand covalently bonded to the surface layer, the metal binding ligand being selected from functionalities comprising at least one of the following bond types: P—O, P=O, S—O, S=O, C—O, C=O, P—N, S—H;
  an ion exchange resin; and
  porous carbon structure.

The pre-concentration disc may thus be made of a porous material or of an ion exchange resin or combinations thereof. When a porous material is used, it comprises a pore surface layer, i.e. the surface of each pore (or at least the surface of a majority of the pores, such as the surface of 80, 90 or 95% of the pores) comprises at least two atomic layers and/or at least one metal binding ligand. Other types of porous materials can also be used. By a porous material it is here meant a material that has an open pore structure. The porosity is defined as the fraction of void within the porous material. The porosity of porous material may range from 4 vol-% to 95 vol-%, The surface area of porous material may range from 10 $m^2/g$ to 1000 $m^2/g$. The porosity and the surface area of porous material may be varied depending on its application areas. The porosity is defined according to ISO 15901-2:2006. The porosity of the material may range from 4, 5, 10, 15, 20, 25, 30, 35, 40, 45, 50, 55, 60, 65 or 70 vol-% up to 20, 30, 40, 45, 50, 55, 60, 65, 70, 75, 80, 85, 90 or 95 vol-%. The surface area of porous material may range from 10, 20, 50, 70, 100, 150, 200, 250, 300, 350, 400, 450, 500, 550, 600, 650, 700, 750, 800, 850, 900, 950, 1000, 1100, 1200, 1500, 2000, 2500, 3000 or 3500 $m^2/g$ up to 100, 150, 200, 250, 300, 350, 400, 450, 500, 550, 600, 650, 700, 750, 800, 850, 900, 950, 1000, 1100, 1200, 1500, 2000, 2500, 3000, 3500 or 4000 $m^2/g$. The intermediate pore width may range from 0.3, 0.5, 0.8, 1, 2, 3, 5, 10, 15, 20, 25, 30, 35, 40, 45, 50, 55, 50, 70, 75, 80, 85, 90, 95, 100, 150, 200, 250, 300, 350 or 400 nm up to 10, 15, 20, 25, 30, 35, 40, 45, 50, 55, 50, 70, 75, 80, 85, 90, 100, 110, 150, 200, 250, 300, 350, 400, 450 or 500 nm or even higher.

Some examples of possible ion exchange resins are sold under tradenames Amberlite™ IRC120 H, Dowex™ 50WX8 and Diphonix™ DP-B500-C-H. The porous material may also be a carbon-based material (i.e. porous carbon structure) in which majority of its mass comprises of carbon, and it may have a surface comprising metal binding ligands. Such carbon-based materials include activated carbon and carbon aerogels.

One example of preparation of the porous material is given below in the Experimental part.

Optionally, in this regard, the porous structure of the pre-concentration disc allows passing of the sample of the aqueous solution therethrough. Furthermore, the porous structure includes the surface layer comprising at least two atomic layers of at least one of the following: carbon, silicon carbide, silicon oxycarbide. Notably, the at least two atomic layers allow stable surface structure and stable covalent bonding of the metal binding ligand with the surface layer. It will be appreciated that the pre-concentration disc comprises of a porous structure to enable bonding of the heavy metals with the metal binding ligands, i.e. the heavy metals can bond at any location within the pre-concentration disc, not only on its outer surface. Furthermore, the metal binding ligand is selected from functionalities comprising at least one of the following bond types: P—O, P=O, S—O, S=O, C—O, C=O, P—N, S—H. Notably, each of the aforementioned functionalities comprise negatively charged monodentate or bidentate ligands to allow bonding of positively charged heavy metal ions therewith. Subsequently, such bonding of the metal content into the porous structure of the pre-concentration disc allows for sorption of metal content therein.

More optionally, the porous structure is a silicon structure. Notably, the porous structure of the pre-concentration disc allows passing of the sample of the aqueous solution therethrough and maximizes surface area of the pre-concentration disc.

The portable assessment kit comprises the means for pumping the sample of the aqueous solution through the opening of the sample container to the first side of the pre-concentration disc and through the pre-concentration disc. Herein, the means for pumping the sample of the aqueous solution is employed to ensure dispensation of the sample of the aqueous solution from the sample container at a predetermined flow rate and in a predetermined quantity. It will be appreciated that the means for pumping ensure a uniform predetermined flow rate to avoid that the metals pass through the pre-concentration disc without sorbing thereon. It is also preferable to use small amounts of liquid to avoid saturation of the pre-concentration disc. Furthermore, the flow rate and the quantity of the liquid flowing through the pre-concentration disc have to be adjusted to ensure sufficient sorption of metals onto the pre-concentration disc and accurate determination of the aqueous metal content of the sample. Additionally, examples of the means for pumping may include, but are not limited to, suction pumps, peristaltic pumps, pneumatic actuators, hydraulic actuators, electrical actuator, and vacuum actuators.

Optionally, the sample container is the syringe and the means for pumping is a syringe pump. As aforementioned, the syringe comprises an opening at its first end and a piston at its second end, wherein the syringe is removably placed in the syringe pump. Subsequently, the syringe pump comprises an actuating arm disposed proximate to the second end of the syringe, wherein the actuating arm is operable to apply a uniform force on the piston to enable the dispensation of the sample of the aqueous solution through the opening and into the disc holder. Consequently, the uniform force applied by the actuating arm ensures a uniform flow rate through the pre-concentration disc. Typically, the speed of movement of the actuating arm is controlled (for example using a stepping motor), based on the diameter of the syringe and the desired flow rate, and then the required duration of this movement is defined based on the required volume to be pumped. Furthermore, the actuating arm applies the uniform force to the piston for a predetermined period of time, wherein the predetermined period of time is calculated based on the predetermined quantity of the sample of the aqueous solution to be passed through the pre-concentration disc. More optionally, the syringe pump is operated using a battery.

Optionally, subsequent to the filtration of the predetermined volume of the sample of the aqueous solution through the pre-concentration disc, the means for pumping the sample of the aqueous solution is employed to push air through the pre-concentration disc. Beneficially, passing the air through the pre-concentration disc enables removal of excess water therefrom and also, ensures complete or partial drying of the pre-concentration disc. Beneficially, such a process of pumping air for drying the pre-concentration disc improves analytical results and reduces time of operation for performing assessment of the sample of the aqueous solution and further reduces cost of operation owing to absence of need of auxiliary drying tools.

Optionally, the portable assessment kit further comprises a pre-filter. The aim of the pre-filter is to remove solids from the sample, but not to concentrate the sample in any other way. Specifically, the pre-filter is arranged in a path of flow of the sample of the aqueous solution. Optionally, the pre-filter is arranged in between the opening of the sample container and the first end of the disc holder. Alternatively, optionally, the pre-filter is arranged inside the disc holder, prior to the pre-concentration disc. Subsequently, the pre-filtered sample of the aqueous solution is received by the pre-concentration disc for analysis thereof. Beneficially, the pre-filter removes (namely, filters) any solid material with a particle size above the pore size of the pre-filter, prior to analysis of metal content therein. Therefore, the pre-filter enhances a quality of analysis result provided by the portable assessment kit, thereby improving a reliability thereof. Optionally, pre-filter can be a filter with 0.45 μm pore size that removes most of the solid substances prior the analysis of the metal contents of the sample.

The portable assessment kit comprises the measurement device for measuring the amount of metals in the pre-concentration disc, the measurement device being arrangeable in connection with the disc holder in such a manner that the first side of the pre-concentration disc is facing the measurement device. Notably, the measurement device refers to a device for measuring physical or chemical quantities. Pursuant to embodiments of the present disclosure, the measurement device is employed to measure the amount of metals in the sample of the aqueous solution. Specifically, the measuring device provides quantitative information regarding amount of metal content present therein. More specifically, the measurement device operates to analyse a nature of atoms present on the pre-concentration disc. It will be appreciated that the metals can be bonded with ligands, on the surface of the material of the pre-concentration disc. Subsequently, the measurement device performs analysis of the sorbed metals present on the pre-concentration disc. Moreover, the first side of the pre-concentration disc, having the most metals thereon, faces the measurement device thereby allowing analysis thereof.

It will be appreciated that the measurement device comprises a receiving portion for enabling a connection of the measurement device with the disc holder. In other words, the measurement device comprises the receiving portion for arranging the disc holder in connection with the measurement device.

Optionally, the disc holder is attached to the measurement device using one of the second part of the disc holder or a combination of the second part and the third part of the filter holder. Specifically, the second part of the disc holder is detached from the first part of the disc holder, and further detachably attached to the receiving portion of the measurement device. It will be appreciated that the receiving portion of the measurement device is designed based on a structure of the second part of the disc holder. Subsequently, the first side of the pre-concentration disc faces the measurement device. Additionally, the third part of the disc holder is attached to the second side of the pre-concentration disc to prevent contamination or breakage of the pre-concentration disc.

Optionally, the measurement device comprises an actuating button to trigger operation thereof. Moreover, optionally, the measurement device comprises a display screen, a memory, and a processing apparatus. Additionally, optionally, the measurement device further comprises at least one operating button, wherein the at least one operating button enables a user of the portable assessment kit to customize parameters or results to be viewed. In another embodiment, the portable assessment kit comprises a touch-sensitive display for giving operation instructions. In an instance, the user may operate the portable assessment kit to determine metal contents of the water. Furthermore, the results obtained by the measurement device is displayed on the display screen of the measurement device.

Optionally, the measurement device comprises an electromagnetic wave generator for emitting a primary electromagnetic beam, and an electromagnetic spectrometer arranged in a path of the electromagnetic beam emitted, scattered or reflected from the disc for measurement thereof. Specifically, the electromagnetic wave generator generates the electromagnetic beam that is emitted from the measurement device to the first side of the pre-concentration disc. It will be appreciated that the emitted electromagnetic beam has defined parameters (such as amplitude, frequency, wavelength, and the like) associated thereto. Additionally, it will be appreciated that the emitted electromagnetic beam will undergo absorption, reflection and refraction when passing through the pre-concentration disc. Moreover, the measurement device comprises the electromagnetic spectrometer to measure parameters associated with electromagnetic beam reflected, scattered or emitted from the pre-concentration disc. It will be appreciated that the parameters associated with the reflected or emitted electromagnetic beam will differ from the parameters associated with the emitted primary electromagnetic beam owing to metal content sorbed into the pre-concentration disc. Subsequently, the parameters associated with the reflected electromagnetic beam are analysed to determine a nature of metals present thereon.

In an example embodiment, the measurement device employs an X-ray fluorescence spectrometer (XRF) for performing the analysis of the pre-concentration disc. Notably, atoms present on the pre-concentration disc are observed when they interact with X-ray radiation. Specifically, a primary X-ray beam, emitted from the electromagnetic wave generator, is incident on the pre-concentration disc. More specifically, some of X-ray beam is scattered and some of X-ray beam is absorbed, based on a nature (such as, chemical constituents, physical construction, and so forth) of the pre-concentration disc. Furthermore, passing the incident X-ray beam through the pre-concentration disc, excites the atoms present in the pre-concentration disc. Subsequently, the excited atoms in the disc emit X-rays along a spectrum of wavelengths that is characteristic of a type of atoms present in the disc. The X-rays emitted by the excited atoms are acquired by the electromagnetic spectrometer to measure, for example, intensity of the emitted X-ray beam from the pre-concentration disc.

Additionally, optionally, the electromagnetic spectrometer further employs a wavelength or energy dispersive spectrometer so as to allow separation of X-ray beam emitted from the pre-concentration disc into characteristic wavelengths for each type of atom (namely, each type of metal) present thereon. Subsequently, the electromagnetic spectrometer analyses each of characteristic wavelengths from the separated X-ray beam to determine quantitatively an amount of each metal present in the pre-concentration disc.

More optionally, the measurement device further comprises a calibration adapter to convert results from the electromagnetic spectrometer for assessment of the sample of the aqueous solution, the adapter being typically executed by a computer. Optionally, the adapter comprises processing system therein to process signals. Additionally, optionally, the adapter in the measurement device converts signals from the electromagnetic spectrometer to intelligible quantitative information. Specifically, the adapter operates to determine an amount of each metal present in the sample of the aqueous solution. Additionally, the adapter operates to determine an amount of each metal present in the aqueous solution based on the amount of each metal present in the pre-concentration disc. In an example, the adapter may operate to graphically depict a level of each metal present in the analysed sample of the aqueous solution. Moreover, the adapter may further flag a warning if an amount of a given metal present therein exceeds an acceptable range for the given metal. It will be appreciated that the adapter is pre-calibrated regarding information relating to such acceptable ranges for different metals.

Additionally, optionally, the measurement device comprises a transceiver module for communicating an assessment result of the aqueous solution, to a database arrangement. Alternatively, optionally, the transceiver module in the measurement device may communicate the signals obtained from the electromagnetic spectrometer to a remote computational unit for processing thereof. Specifically, the transceiver module communicates the assessment result (namely, the quantitative analysis of the sample of the aqueous solution and/or the qualitative analysis of the sample of the aqueous solution) to the database arrangement. In another embodiment, the measurement data is sent without any analysis and the analysis is thus performed elsewhere than in the assessment kit. It will be appreciated that such database arrangement may be a cloud storage, a hardware storage, or a combination thereof. Moreover, the transceiver module is communicably coupled with the database arrangement, via a data communication network.

The portable assessment kit may further comprise the portable case for containing the sample container, the disc holder, the pre-concentration disc, the means for pumping and the measurement device. Specifically, such portable case is employed so as to safely transfer the sample container, the disc holder, the pre-concentration disc, the means for pumping and the measurement device for enabling on-site operation thereof. Optionally, the portable case may have a dedicated cavity for each of the components of the portable assessment kit. Moreover, optionally, the portable case has a rigid external frame for protection against thrust and further has several layers of cushioning arrangements so as to absorb shock and pressure acting thereupon, thereby protecting the components of the portable assessment kit. In another embodiment, the portable case may be a backpack. In yet another embodiment, the parts of the kit can be separately portable (for example in a pocket or similar) and assembled on the measurement site.

In an exemplary implementation, the portable assessment kit is employed for measuring metal content for an aqueous solution from a water body (namely, a lake, a river, a pond, reservoir, pool and the like). The sample is received from the aqueous solution, wherein the sample is contained in the sample container. Specifically, the opening at the first end of the sample container, for example, a syringe is immersed in the aqueous solution and a piston thereof is withdrawn so as to obtain the sample of the aqueous solution. Subsequently, upon receiving the sample, the disc holder comprising the pre-concentration disc is detachably attached to the opening at the first end of the sample container. Specifically, the first part of the disc holder having the first end is attached with the opening at the first end of the sample container. Moreover, the pre-concentration disc is arranged between the second part and the third part of the disc holder. Moreover, the second part of the disc holder is detachably attached to the first part and the third part is detachably attached to the second part. It will be appreciated that the first side of the pre-concentration disc, faces the second part of the disc holder and the second side of the pre-concentration disc faces the third part of the disc holder. Additionally, the piston of the sample container is placed in contact with the means for pumping the sample, wherein the means for pumping the sample is pre-adjusted to apply a force onto the piston to pump a predetermined quantity of the sample at a predetermined flow rate. Such pre-adjustment of the means for pumping is done based on a nature (such as dimensions, material of construct, and so forth) of the pre-concentration disc. Furthermore, the means for pumping applies a force onto the piston of the storage container to pump the sample from the storage container to the disc holder. Consequently, the sample is pushed from the opening of the sample container to the pre-concentration arrangement and further to the first side of the pre-concentration disc and through the pre-concentration disc. It will be appreciated that the metal content in the sample is sorbed partially or completely onto the pre-concentration disc. Moreover, the sample container further pumps air to the pre-concentration disc, through the disc holder, so as to allow partial or complete drying of the pre-concentration disc. Furthermore, the second part of the disc holder is removed from the first part thereof (and hence, from the opening of the sample container) and further attached to the receiving portion of the measurement device. Specifically, the first side of the pre-concentration disk faces the receiving portion of the measurement device. The measurement device performs X-ray fluorescence spectroscopy to identify nature of atoms and a concentration thereof, present in the pre-concentration disc. Typically, the nature of atoms is utilized to identify the type of metal. Moreover, based on results of the X-ray fluorescence measurement of the pre-concentration disc, the amount of each metal is calculated for the aqueous solution. Furthermore, the measuring device displays the amount of each metal present in the aqueous solution in a tabular and graphical format and further communicates the calculated amounts of each metal to the database arrangement, wherein the database arrangement is implemented by way of a cloud storage arrangement.

The present disclosure also relates to the method as described above. Various embodiments and variants disclosed above apply mutatis mutandis to the method.

According to one embodiment, the step of obtaining a sample in a sample container may be a step where a sample is pumped from a water body such as a lake, a river or a sea to the portable assessment kit. In such a case, the pipe or tube acts as a sample container. This embodiment is particularly useful if the kit is left in place for an extended period of time and functions automatically. In such a case, the kit may also comprise means for communicating the measurement results to a remote database or similar.

Optionally, the method comprises using the pre-concentration disc comprising of a material selected from a group of:

a porous structure including a pore surface layer, wherein the pore surface layer comprises at least two atomic layers of at least one of the following: carbon, silicon carbide, silicon oxycarbide;

a porous structure including a pore surface layer, wherein the pore surface layer comprises at least one metal binding ligand covalently bonded to the surface layer, the metal binding ligand being selected from functionalities comprising at least one of the following bond types: P—O, P=O, S—O, S=O, C—O, C=O, P—N, S—H;

a porous carbon structure; and an ion exchange resin.

Optionally, the porous structure is a silicon structure. The method may comprise employing a syringe as the sample container and a syringe pump as the means for pumping. The method also comprises detachably attaching the disc holder to the opening of the sample container, via a first part of the disc holder having the first end.

The method further comprises arranging the pre-concentration disc between a second part of the disc holder and a third part of the disc holder in a manner that the first side of the pre-concentration disc is facing the second part of the disc holder and the second side of the pre-concentration disc is facing the third part of the disc holder. More optionally, the method comprises attaching the disc holder to the measurement device using the second part of the disc holder.

Experimental Part

Figure 2:
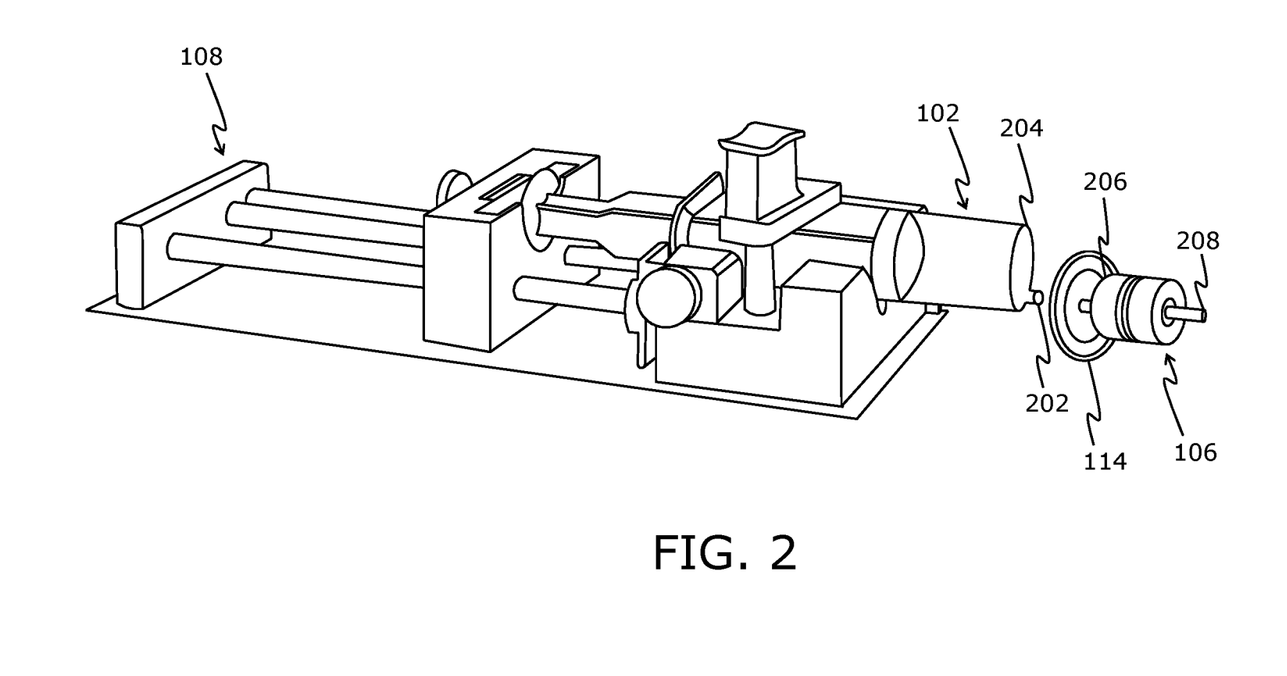
FIG. 2 illustrates a perspective view of a sample container, a disc holder, a concentration disc and means for pumping of the portable assessment kit of FIG. 1, in accordance with an embodiment of the present disclosure.

A portable assessment kit was tested with two different water samples, and the results were compared to test results obtained with a laboratory equipment testing the same metals. The portable assessment kit used in the tests is as shown in FIG. 2. The preconcentration disc comprises of porous silicon structure with a surface layer produced by carbonization of acetylene gas on the surface and a metal binding bisphosphonate molecule attached on the surface layer (prepared as explained below). The laboratory equipment was an ICP-MS-device (Inductively coupled plasma mass spectrometry, Perkin-Elmer Nexion 350D-AMS).

Both samples were from a natural water body contaminated with metals by industrial activity. The volume of the sample was 10 ml and flow rate of 1 ml/min was used for both samples.

The detected metals (copper, zinc, lead, nickel and manganese) and their amounts in ppb (parts per billion) are given in Tables 1 and 2 below. As can be seen, the results of the portable assessment kit (marked with PAK) compare well with the laboratory equipment (marked with ICPMS). Amounts of metals below 50 ppb were considered to be under the detection limit in this particular example.

TABLE 1

| | Metal | | | | | |
|---|---|---|---|---|---|---|
| | Cu (ppb) | | Zn (ppb) | | Pb (ppb) | |
| Technique | | | | | | |
| | PAK | ICPMS | PAK | ICPMS | PAK | ICPMS |
| Sample 1 | <50 | 3.4 | 86 | 64 | <50 | <0.50 |
| Sample 2 | 155 | 172 | 1995 | 1650 | <50 | <0.50 |

TABLE 2

| | Metal | | | |
|---|---|---|---|---|
| | Ni (ppb) | | Mn (ppb) | |
| Technique | | | | |
| | 3AW | ICPMS | 3AW | ICPMS |
| Sample 1 | <50 | 15 | 1353 | 1790 |
| Sample 2 | 544 | 640 | <50 | 2.0 |

Preparation of Porous Silicon by Electrochemical Etching

P+-type silicon wafer was electrochemically etched in electrolyte comprising 1:1 mixture of hydrofluoric acid (HF, 38-40%) and ethanol (99.6%). The wafer acted as an anode and a platinum electrode was immersed in the electrolyte as a cathode. Current density of 30 mA/cm$^2$ was applied for 40 min. Parallel pores on top of the wafer were formed. Afterwards, two 200 mA/cm$^2$ current pulses lasting for 4 s were applied to remove the porous silicon (PSi) layer from the surface. PSi layers were collected and dried afterwards. Properties of the formed material were characterized by N$_2$ adsorption (Micromeritics Tristar II); porosity was 75 vol-%, surface area 230 m$^2$/g and pore diameter 9.7 nm. The PSi layers were ground in a planetary ball mill (Fritsch Pulverisette 7) and sieved to particle size (diameter) of under 25 μm.

Passivation by Carbonization

The PSi surface can be passivated with thermal carbonization in a tube oven. 0.5 g of PSi particles was placed to a quartz tube and oxygen was removed by nitrogen purging (1 l/min) for 30 min. Acetylene was introduced to the particles by purging the sample with a mixture of nitrogen/acetylene (1 l/min both) for 15 min. Subsequently, sample was heated at 500° C. under nitrogen/acetylene purge (1 l/min both) for 15 min. The sample was cooled to room temperature under nitrogen purge, after which acetylene was adsorbed on the surface using a mixture of nitrogen and acetylene gases both at flow rate of 1 l/min. The acetylene purge was then cut off and the sample was heated at 820° C. for 10 min, after which the sample was cooled down to room temperature under nitrogen atmosphere. This resulted in silicon carbide/carbon type of chemical structure with free radicals on the surface. The chemistry was confirmed with Fourier transform infrared spectroscopy (FTIR) and solid state nuclear magnetic resonance spectrometry. The radicals may easily react with moisture and air forming silicon oxycarbides on the surface. The material was kept under inert atmosphere after the carbonization in order to prevent silicon oxycarbide formation, and in order to enable further functionalization.

Bisphosphonate Functionalization

A bisphosphonate BP1 with protective SiMe$_3$ groups was conjugated on the surfaces of thermally carbonized porous silicon. 250 mg of bisphosphonate (BP1) was dissolved in 10 ml of mesitylene and the solution was bubbled with nitrogen for 15 min in order to remove oxygen from the solution. Afterwards, under nitrogen atmosphere, the solution was transferred onto the PSi particles carbonized as described in above. The sample was placed in the oven at a temperature of 120° C. for overnight treatment. Afterwards, the sample was cooled down and washed with methanol and ethanol in order to remove excess BP1 molecules and to remove protective groups (SiMe$_3$) of the BP1 molecules. The BP1 amount conjugated to the carbonized PSi surface was quantified to be 2.5% (w/w) with TG.

BP1 n = 8

Preparation of Preconcentration Disks 420 mg of the BP1 conjugated carbonized PSi particles, having a diameter below 25 μm, 21 mg of sodium carboxymethyl cellulose (low viscosity) and 21 mg of polyacrylic acid (100 kDa) were mixed with 1.2 ml of water to form a slurry, which was spread on Whatmann Grade 3 filter paper with a doctor blade, which was set on 240 μm from the filter paper surface. The slurry with the filter paper was heated to 120° C. in vacuum for overnight to remove water and crosslink the polymers. This resulted in a smooth and fixed particle layer on top of the filter paper, forming a filter system. Pre concentration disks having a diameter of 12 mm were cut from the filter system.

DETAILED DESCRIPTION OF THE DRAWINGS

Figure 1:
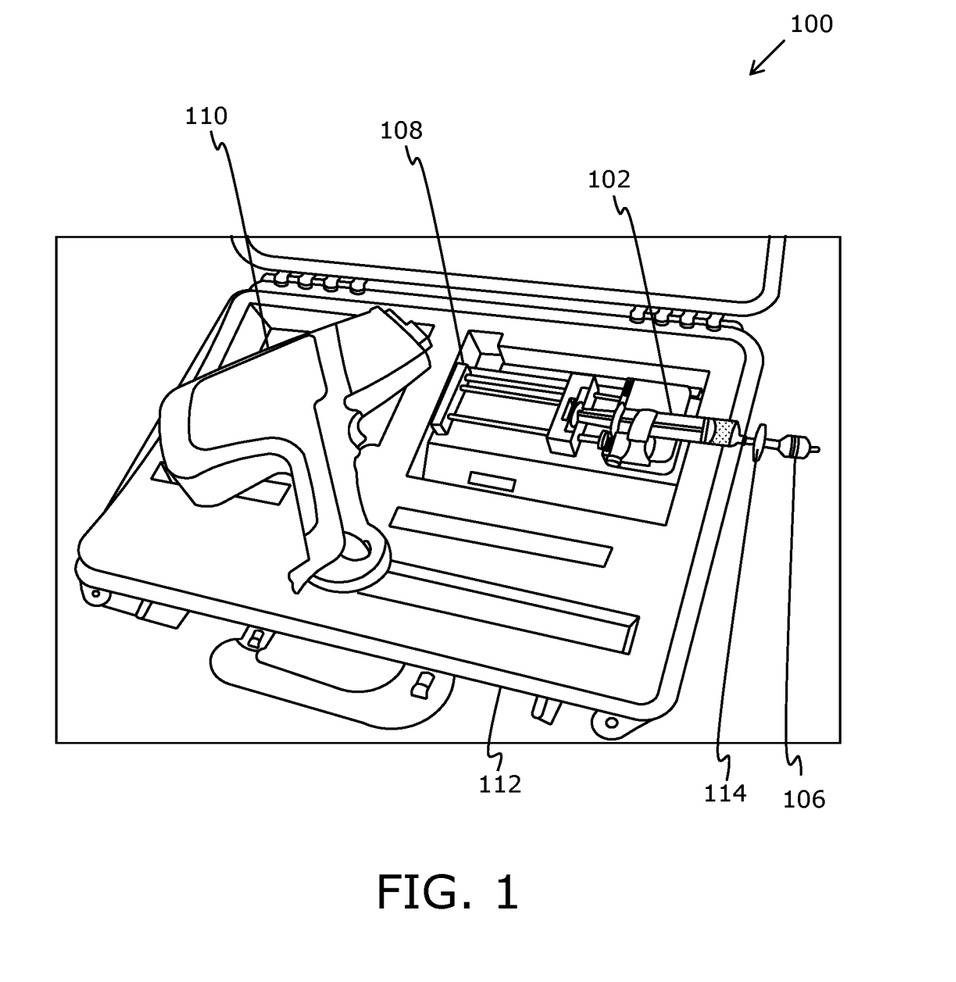
FIG. 1 illustrates a perspective view of a portable assessment kit for measuring metal content of an aqueous solution, in accordance with an embodiment of the present disclosure.

Referring to FIG. 1, illustrated is a perspective view of a portable assessment kit 100 for measuring metal content of an aqueous solution, in accordance with an embodiment of the present disclosure. The portable assessment kit 100 comprises a sample container 102 for containing a sample of the aqueous solution to be assessed and a disc holder 106, with a pre-concentration disc for collecting metals arranged therein (and thus not visible in the FIG.). The FIG. further shows a pre-filter 114 arranged in between the opening of the sample container and the first end of the disc holder. The portable assessment kit 100 comprises a means for pumping 108 the sample of the aqueous solution through the pre-concentration disc from the sample container 102. The portable assessment kit 100 comprises a measurement device 110 for measuring amount of metals in the pre-concentration disc, wherein the measurement device 110 is arrangeable in connection with the disc holder 106. Moreover, the portable assessment kit 100 comprises a portable case 112 for containing the sample container 102, the disc holder 106, the means for pumping 108 and the measurement device 110.

Referring to FIG. 2, illustrated is a perspective view of the sample container 102, the disc holder 106 and the means for pumping 108 of the portable assessment kit 100 of FIG. 1, in accordance with an embodiment of the present disclosure. As shown, the sample container 102 for containing a sample of the aqueous solution to be assessed comprises an opening 202 at its first end 204 for receiving and dispensing the sample. The disc holder 106 has a first end 206, and a second end 208 opposite to the first end 206, wherein the first end 206 of the disc holder 106 is detachably attached to the opening 202 of the sample container 102. Furthermore, the pre-concentration disc (not visible in the FIG.) for collecting metals in the aqueous solution is arrangeable in the disc holder 106. Moreover, the means for pumping 108 is operable to pump the sample of the aqueous solution through the opening 202 of the sample container 102 to the first side of the disc holder 206 and through the pre-concentration disc inside the disc holder 106, when the disc holder 106 is attached to the opening 202 of the sample container 102.

Figure 3:
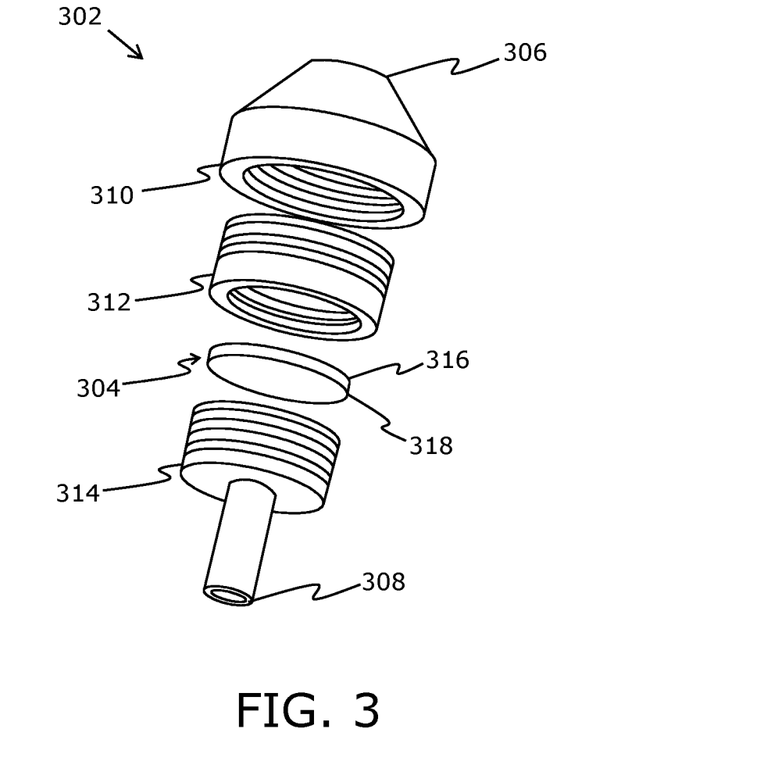
FIG. 3 illustrates an exploded view of a disc holder and the metal collecting disc of a portable assessment kit, in accordance with an embodiment of the present disclosure.

Referring to FIG. 3, illustrated is an exploded view of a disc holder 302 of the portable assessment kit (such as the portable assessment kit 100 of FIG. 1) and the metal collecting pre-concentration disc, in accordance with an embodiment of the present disclosure. The pre-concentration disc 304 is arrangeable in the disc holder 302. As shown, the disc holder 302 having a first end 306 comprises a first part 310 for detachably attaching the disc holder 302 to the opening of the sample container (such as the opening 202 of the sample container 102 of FIG. 2). As shown, the disc holder 302 further comprises a second part 312 and a third part 314, wherein the pre-concentration disc 304 is arranged between the second part 312 and the third part 314. The pre-concentration disc 304 has a first side 316 facing the first end 306 of the disc holder 302, and a second side 318 opposite to the first side 316, the second side facing the second end 308 of the disc holder 302. The third part 314 of the disc holder 302 comprises the second end 308 of the disc holder 302.

Figure 4:
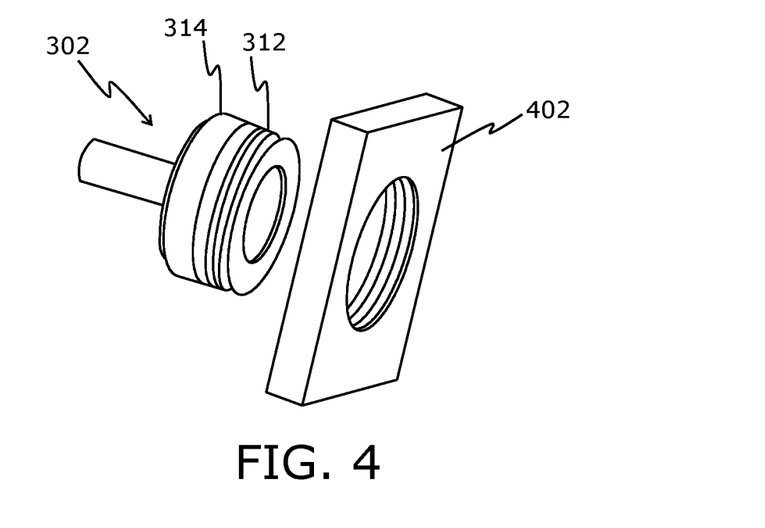
FIG. 4 illustrates an arrangement of second part and third part of a disc holder with a receiving portion of a measurement device, in accordance with an embodiment of the present disclosure.

Referring to FIG. 4, illustrated is an arrangement of second part 312 and third part 314 of the disc holder 302 with a receiving portion 402 of the measurement device (such as the measurement device 110 of FIG. 1), in accordance with an embodiment of the present disclosure. Notably, the measurement device comprises the receiving portion 402 for arranging the disc holder 302 in connection with the measurement device 110. Furthermore, the disc holder 302 is attached to receiving portion 402 of the measurement device 110 using the second part 312 of the disc holder 302. In particular, the measurement device 110 is arrangeable in connection with the disc holder 302 in such a manner that the first side of the pre-concentration disc 304 (such as the first side 316 as shown in FIG. 3) is facing the measurement device 110. In this FIG., the measurement device 110 is as shown in FIG. 1.

Figure 5A:
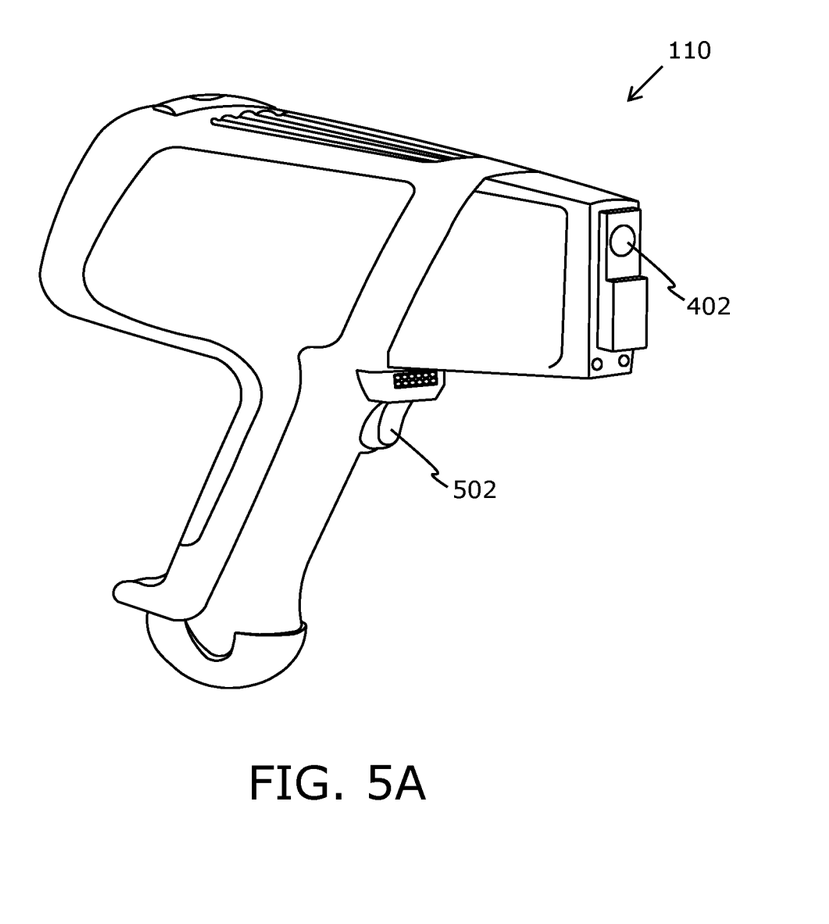
FIGS. 5A and 5B illustrate different perspective views of a measurement device, in accordance with an embodiment of the present disclosure.
Figure 5B:
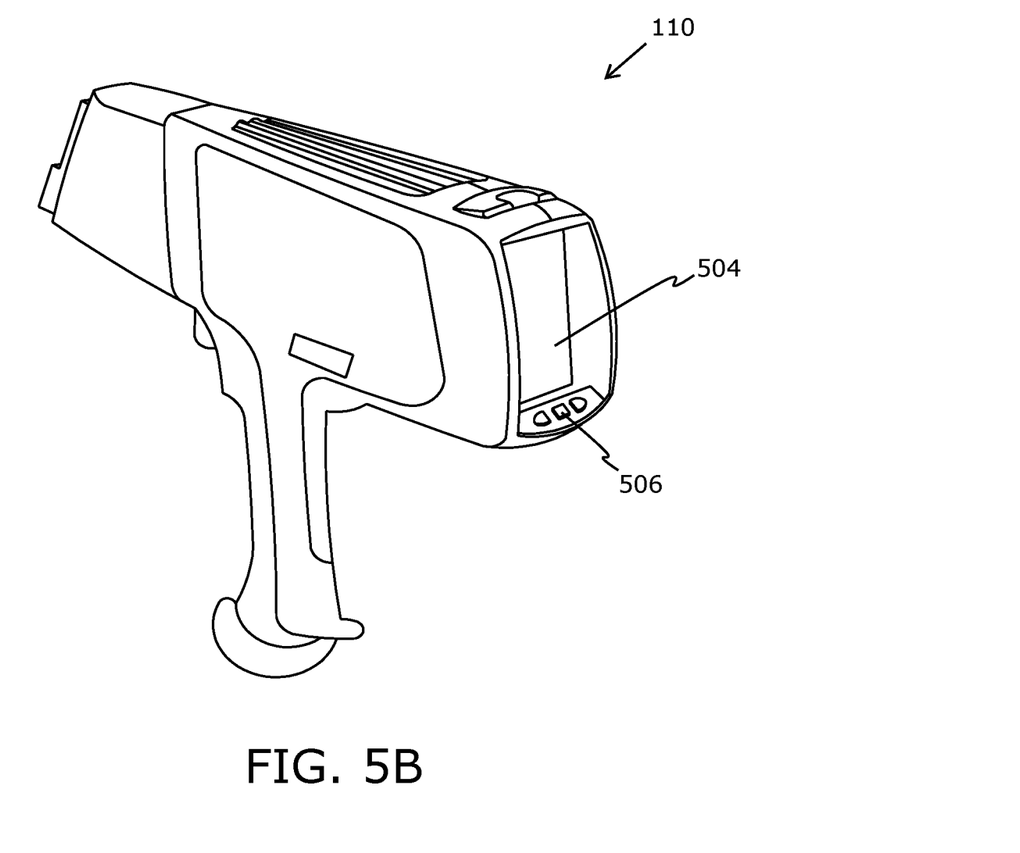

Referring to FIGS. 5A and 5B, illustrated are different perspective views of the measurement device 110, in accordance with an embodiment of the present disclosure. As shown in FIG. 5A, the measurement device 110 comprises a receiving portion 402 for enabling a connection of the measurement device 110 with the disc holder (such as the disc holder 106 of FIG. 1). Furthermore, the measurement device 110 comprises an actuating button 502 for triggering the operation of the measurement device 110. As shown in FIG. 5B, the measurement device 110 further comprises a display screen 504 to show analytical data relating to the metal content of the aqueous solution flown through the pre-concentration disc, and at least one operating button (such as the operating button 506) to enable a user of the portable assessment kit to customize parameters or results to be viewed.

Figure 6:
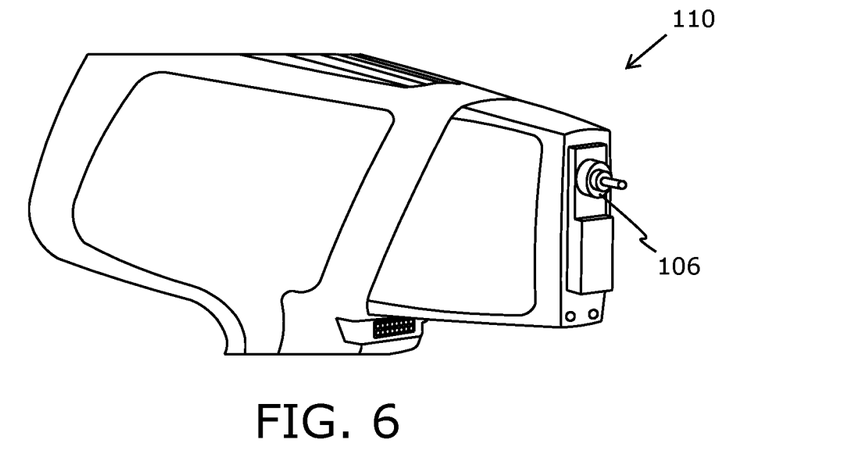
FIG. 6 illustrates a perspective view of a measurement device arranged in connection with a disc holder, in accordance with an embodiment of the present disclosure.

Referring to FIG. 6, illustrated is a perspective view of the measurement device 110 arranged in connection with the disc holder 106 (from which the first part indicated with reference 310 in FIG. 3 has been removed), in accordance with an embodiment of the present disclosure. Herein, the disc holder 104 is arranged in connection with the measurement device 110 using the receiving portion of the measurement device (depicted as the receiving portion 402 in FIG. 5A).

Figure 7:
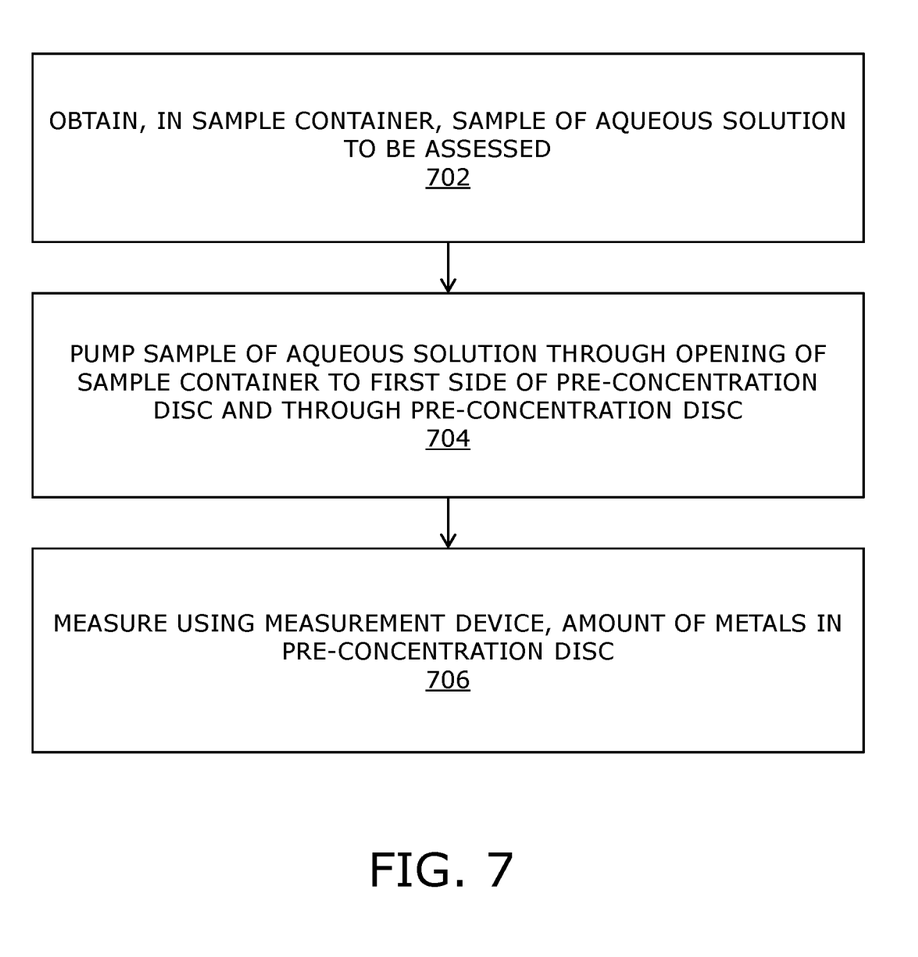
FIG. 7 illustrates steps of a method for measuring metal content of an aqueous solution, in accordance with an embodiment of the present disclosure.

Referring to FIG. 7, illustrated are steps of a method for measuring metal content of an aqueous solution, in accordance with an embodiment of the present disclosure. The method is implemented via a portable assessment kit (such as the portable assessment kit 100 of FIG. 1). At a step 702, a sample of the aqueous solution to be assessed is obtained in a sample container. The sample container comprises an opening at its first end for receiving the sample. At a step 704, the sample of the aqueous solution is pumped through the opening of the sample container to a first side of a pre-concentration disc and through the pre-concentration disc. The pre-concentration disc having a first side, and a second side opposite to the first side, is arrangeable in a disc holder. The disc holder having a first end, and a second end opposite to the first end, is detachably attached to the opening of the sample container, via the first end of the disc holder. At a step 706, amount of metals in the pre-concentration disc is measured using the measurement device. The measurement device is arrangeable in connection with the disc holder in such a manner that the first side of the pre-concentration disc is facing the measurement device.

The steps 702, 704, and 706 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A portable assessment kit for measuring metal content of an aqueous solution, the portable assessment kit comprising:
   a sample container for containing a sample of the aqueous solution to be assessed, wherein the sample container comprises an opening at its first end for receiving the sample;
   a disc holder having a first end, and a second opposite to the first end, wherein the first end of the disc holder is detachably attached to the opening of the sample container;
   a permeable pre-concentration disc for collecting metals, the pre-concentration disc having a first side, and a second side opposite to the first side, and being arrangeable in the disc holder;
   means for pumping the sample of the aqueous solution through the opening of the sample container to the first side of the pre-concentration disc and through the pre-concentration disc; and
   measurement device for measuring amount of metals in the pre-concentration disc, the measurement device being arrangeable in connection with the disc holder in such a manner that the first side of the pre-concentration disc is facing the measurement device,
   wherein the disc holder comprises a first part having the first end for detachably attaching the disc holder to the opening of the sample container, and the disc holder further comprises a second part and a third part, wherein the pre-concentration disc is arranged between the second part and the third part in a manner that the first side of the pre-concentration disc is facing the second part of the disc holder and the second side of the pre-concentration disc is facing the third part of the disc holder.

2. The portable assessment kit according to claim 1, further comprising a portable case for containing the sample container, the disc holder, the pre-concentration disc, the means for pumping and the measurement device.

3. The portable assessment kit according to claim 1, wherein the pre-concentration disc comprises of a material selected from a group of:
   a porous structure including a pore surface layer, wherein the pore surface layer comprises at least two atomic layers of at least one of the following: carbon, silicon carbide, silicon oxycarbide;
   a porous structure including a pore surface layer, wherein the pore surface layer comprises at least one metal binding ligand covalently bonded to the surface layer, the metal binding ligand being selected from functionalities comprising at least one of the following bond types: P—O, P=O, S—O, S=O, C—O, C=O, P—N, S—H;
   an ion exchange resin; and
   a porous carbon structure.

4. The portable assessment kit according to claim 3, wherein the porous structure is a silicon structure.

5. The portable assessment kit according to claim 1, wherein the sample container is a syringe and the means for pumping is a syringe pump.

6. The portable assessment kit according to claim 1, wherein the disc holder is attached to the measurement device using one of the second part of the disc holder or a combination of the second part and the third part (314) of the disc holder.

7. The portable assessment kit according to claim 1, wherein the measurement device comprises an electromagnetic wave generator for emitting an electromagnetic beam, and an electromagnetic spectrometer arranged in a path of the electromagnetic beam emitted, scattered or reflected from the disc for measurement thereof.

8. The portable assessment kit according to claim 7, wherein the measurement device further comprises an adapter to convert results from the electromagnetic spectrometer for assessment of the aqueous solution.

9. The portable assessment kit according to claim 1, wherein the measurement device comprises a transceiver module for communicating an assessment result of the aqueous solution, to a database arrangement.

10. A method for measuring metal content of an aqueous solution, wherein the method is implemented via a portable assessment kit, the method comprising:
    obtaining, in a sample container, a sample of the aqueous solution to be assessed, wherein the sample container comprises an opening at its first end for receiving the sample;
    detachably attaching a disc holder to the opening of the sample container, via a first part of the disc holder having a first end of the disc holder, wherein the disc holder has the first end and a second end opposite to the first end;
    arranging a permeable pre-concentration disc between a second part of the disc holder and a third part of the disc holder in a manner that a first side of the pre-concentration disc is facing the second part of the disc holder and a second side of the pre-concentration disc is facing the third part of the disc holder, wherein the pre-concentration disc having the first side and the second side opposite to the first side is arrangeable in the disc holder;
    pumping the sample of the aqueous solution through the opening of the sample container to the first side of the permeable pre-concentration disc and through the pre-concentration disc; and
    measuring, using a measurement device, amount of metals in the pre-concentration disc, the measurement device being arrangeable in connection with the disc holder in such a manner that the first side of the pre-concentration disc is facing the measurement device.

11. The method according to claim 10, further comprising attaching the disc holder to the measurement device using one of the second part of the disc holder or a combination of the second part and the third part.

* * * * *